(12) United States Patent
Goode, Jr.

(10) Patent No.: US 9,930,914 B2
(45) Date of Patent: Apr. 3, 2018

(54) SEAMLESS ORAL POUCH PRODUCT

(71) Applicant: Read Fisher Goode, Jr., Richmond, VA (US)

(72) Inventor: Read Fisher Goode, Jr., Richmond, VA (US)

( * ) Notice: Subject to any disclaimer, the term of this patent is extended or adjusted under 35 U.S.C. 154(b) by 130 days.

(21) Appl. No.: 14/959,017

(22) Filed: Dec. 4, 2015

(65) Prior Publication Data

US 2016/0165953 A1    Jun. 16, 2016

Related U.S. Application Data

(60) Provisional application No. 62/092,290, filed on Dec. 16, 2014.

(51) Int. Cl.
*A24F 23/02* (2006.01)
*A61K 9/00* (2006.01)

(52) U.S. Cl.
CPC ............. *A24F 23/02* (2013.01); *A61K 9/009* (2013.01)

(58) Field of Classification Search
CPC .......... A01K 15/02; B65D 3/02; A61K 9/009; A24F 23/00; A24F 23/03
USPC ........................................................ 131/352
See application file for complete search history.

(56) References Cited

U.S. PATENT DOCUMENTS

| 4,449,983 A | 5/1984 | Cortese et al. |
| 6,162,516 A | 12/2000 | Derr |
| 2011/0303232 A1 | 12/2011 | Williams |
| 2012/0031414 A1* | 2/2012 | Atchley ............... A24B 13/00 131/118 |
| 2012/0128734 A1 | 5/2012 | Hubinette et al. |
| 2014/0083438 A1 | 3/2014 | Sebastian et al. |

OTHER PUBLICATIONS

Notification of Transmittal of International Search Report and the Written Opinion of the International Searching Authority; dated Feb. 9, 2016; 7 pages.
PCT Application Serial No. PCT/US2015/063985; Notification of Transmittal of International Preliminary Report on Patentability; dated Jun. 29, 2017; 5 pages.

* cited by examiner

*Primary Examiner* — Michael H. Wilson
*Assistant Examiner* — Russell E Sparks
(74) *Attorney, Agent, or Firm* — John H. Thomas, P.C.

(57) ABSTRACT

An oral pouch product has no seams or fewer seams than conventional pouch products. The pouch includes a seamless or single seam tube of a hosiery web material. An elastomeric thread is placed inside the tubular enclosure. One end of the tube is sealed and connected to one end of the elastomeric thread. A filling material, in one example including tobacco products or other plant materials, is also placed inside the tubular enclosure. The second end of the tubular enclosure is then fixed and connected to a stretched end of the elastomeric thread. The thread and attached ends of the enclosure are then sheared away and simultaneously released so that the ends of the tube are drawn inside the tubular space of the tubular enclosure.

16 Claims, 5 Drawing Sheets

SEAMLESS ORAL POUCH PRODUCT

This application claims the benefit of U.S. Provisional Patent Application No. 62/092,290 filed Dec. 16, 2014, which is incorporated by reference herein in its entirety.

The field of the invention is oral pouch products for consumer use. Specifically, the oral pouch described herein has no seams or fewer seams than existing oral pouch products. The pouch contains, in one example, a filling material including tobacco products.

BACKGROUND

"Dipping" snuff is the original method of using smokeless tobacco. A user inserts his thumb and forefinger into a can of snuff, pinches the desired amount, and then places it between his lower front cheek and gum. The snuff is in direct contact with the gum and lip tissues. Because of the size of its particles and its moisture content, when squeezed between the cheek and gum, a pinch of snuff molds into a given shape and generally stays together in that shape during use only resulting in a small number of single particles traveling on their own elsewhere in the mouth. Best practice is to not leave the dip in one place during use as this will cause irritation, but instead to frequently move the dip to different areas of the mouth between the lower and upper gums and lips.

Another smokeless tobacco, snuss, is more powder-like. It is pulverized and generally has a lower moisture content than snuff, so it does not mold well in the mouth and travels about. When the "dipping" method is used with snuss, which is common in Europe, it is often placed between the upper lip and gum, which is different from the usual North American tradition of placing it between the lower lip and gum. A mess is created because the snuss will not remain just between the cheek and gum; it travels uncontrollably throughout the mouth.

Snuss and snuff tobacco products are often packaged in single-serving, fibrous, "pouches" made from a "tea bag" cellulose fiber type material. These "pouches" retain 100% of the snuff or snuss inside of the pouch keeping the tobacco from contacting the oral tissue directly and keeping the tobacco from traveling about in the mouth. The tea-bag pouch generally reduces mouth irritation since it keeps the tobacco product from directly contacting any oral tissue, yet allowing the saliva to leach into the pouch and mix with the tobacco to create "juice" which then leaches out of the pouch and travels over the tongue to the enjoyment of its user. Unlike a plain dip of snuff, a pouch allows its user to remove the pouch from the mouth and have no residual particles remaining in the oral cavity. A snuff dipper has to rinse the mouth with a liquid after removing the dip or generate excessive saliva to wash the remaining loose particles of snuff from the mouth by expectorating. A pouch can be removed, stored and then re-used later. A dip of snuff is generally a one-time use and then is discarded.

The very commonly used "tea bag" type pouch requires its user to generate a sufficient amount of saliva to dampen the pouch so that the saliva can then be wicked through the fibrous material. Once the "tea bag" is fully saturated, the tobacco inside then absorbs saliva through a wicking process until saturated. Once the tobacco is dampened with saliva, the pouch is then squeezed between the lip and gum, so that tobacco juice is excreted and the chemicals therein are absorbed by the gum and lip tissue. When a snuff filled pouch is used, often excess saliva is generated causing the user to expectorate. When a snuss filled pouch is used, the user is less likely to desire to expectorate because of the differences of the chemical makeup of snuss versus snuff and their respective effects on the salivary glands.

The tea bag material is paper-like and is not very flexible. It is difficult for the user to alter its shape. It also has a sealed flap at either end and often has a seam along its long side. These seams are created by overlapping two pieces of the tea bag material and sealing them. These seals create edges and an additional layer of material that requires more saliva to dampen and can be uncomfortable to the user. With these three seams (two on the ends and one along the side) a significant chance exists, and often occurs, for seam failure. When any one seam fails, the snuff or snuss filling leaves the pouch and enters the mouth floating freely about to the dismay of the user. The longer a pouch is used the higher the likelihood that the cellulose material itself fails. After only 15 minutes of use it is common for a pouch to rupture. A pouch failure results in its user very inconveniently having to abandon the pouch and rinse or spit out all of the loose snuff or snuss from the mouth. Discretion is highly valued by smokeless tobacco users. Eliminating pouch failure could be a commercial advantage over the conventional fibrous pouch.

Since the tea bag material must first be dampened by the user before the tobacco juice can be enjoyed, the flow of saliva in and out of the pouch is much slower than with a dip. It also takes much longer for nicotine from the tobacco inside of the pouch to create a sensation in its user than with a dip of snuff which is in direct contact with oral tissues. The lack of elasticity of the pouch does not allow the user to form it to fit the particular part of the oral cavity desired.

The tobacco inside of the pouch becomes compressed as it hydrates during use from the outside surface slowly towards the center. The tobacco in the center of the pouch is the last portion to be hydrated. Since the tea bag pouch is relatively inflexible, the user cannot reshape and compress the tobacco so that all of the tobacco reaches the same moisture content quickly. The tobacco within a pouch does not move around easily within the pouch. It generally stays in its same form throughout use. Once the tobacco has hydrated to the user's desire, its releases its flavors and chemicals. After these flavors and chemicals are released, the tobacco has to be squeezed even more and moved about in the mouth to get all of the flavors and chemicals out of the tobacco. After a period of use, most of the flavors and chemicals have leached out and the tobacco is no longer of use to the user.

A snuff user has the freedom to form and squeeze the pouchless dip of snuff throughout the dipping process so that approaching 100% of the tobacco is hydrated quickly and that nearly all of the flavors, nicotine and other chemicals are excreted immediately into the user's mouth. In moving a dip about in the mouth with the tongue, it is flipped, turned and folded over and upon itself while between the lower lip and gum. This "dipping" action quickly exposes all of the dip, not just its outer surfaces to the oral tissues. The rate of nicotine absorption into the bloodstream is significantly faster with a dip than with a pouch.

Once dampened, the tea bag pouch becomes very slippery with a coefficient of friction less than that of the adjacent gum and lip tissue resulting in the pouch uncontrollably "swimming" easily around between the lip and gum. The surface of a packed dip of snuff between the cheek and gum has a lower coefficient of friction than a pouch and will remain in a specific location between the cheek and gum considerably easier and longer than with a pouch. Due to this lower coefficient of friction and to the textured surface of a dip of snuff, a dip "sticks" via molecular adhesion somewhat to the tissue it adjoins where the user of a pouch has to put forth additional efforts in contracting the lip to maintain a certain position. For instance, a snuff user can typically cough or sneeze and have the dip remain fully intact and in place. However, coughing or sneezing will frequently dislodge a pouch out of the oral cavity to the dismay of the user and often the surprise of unknowing bystanders.

Discretion is often a critical element of smokeless tobacco usage. It is one of many benefits of using smokeless versus smoking tobacco and is often the most important difference between the two. The use of tobacco has been demonized in modern culture and is often frowned upon. Discretion is very difficult to achieve for smokers. With an oral embodiment that does not bulge the lip, however, a dip or pouch remains fully enclosed and concealed in the mouth and out of any view of bystanders and coworkers. It will hopefully stay in place during unexpected sneezes and coughs ensuring absolute confidentiality of the user's usage which is of critical importance in many business and social situations where the user's reputation is at stake.

SUMMARY

Accordingly, it is an object of the present invention to describe a more friendly and efficient oral pouch product that overcomes the foregoing problems and challenges with existing pouch products.

In one example an oral pouch product comprises a web defining an enclosure, wherein the enclosure has a tubular shape. A loose filling material is inside the enclosure, where the filling material comprises a plant material. The web is comprised of a hosiery material, and each end of the tubular enclosure is sealed. An elastomeric thread is positioned inside the tubular enclosure, wherein the elastomeric thread is fixed on a first end to the tubular enclosure, and the elastomeric thread is fixed on a second end opposite the first end to the second end of the tubular enclosure. The sealed first and second ends of the tubular enclosure are closer together than a length of the tubular enclosure, whereby the sealed ends of the tubular enclosure are retained inside the tubular shape of the enclosure. The web may be seamless. The web may be comprised of nylon and/or spandex. The elastomeric thread may be comprised of natural rubber. The filling material may be comprised of a plant material selected from the group consisting of tobacco, coconut husks, vegetable fibers, tea, herbs, spices, coffee, fruits, marijuana, marijuana derivatives and combinations thereof. The tobacco product may be selected from the group consisting of snuff and snuss. The filling material may also be comprised of non-plant material selected from the group consisting of nicotine, caffeine, decarbolized THC, flavorings and pharmaceuticals. The tubular enclosure may have a substantially round cross section width of about ¼ inch to ¾ of an inch in diameter, or alternatively about ⅜ or ½ of an inch in diameter. The longitudinal length of the tubular enclosure may be about ½ to 2 inches, or alternatively about ¾ to 1 inch. The dry weight of the filling material may be about 50 mg to 500 mg, or alternatively about 100 mg to 500 mg.

BRIEF DESCRIPTION OF THE DRAWINGS

FIG. 5 is a side view of an empty tubular hosiery sleeve with an elastic thread extending through the center thereof.

FIG. 6 is a side view of the tube of hosiery material that is closed and sealed on one end.

FIG. 7 is a perspective view of a tin of tobacco and a straw used to pick up amounts of that tobacco.

FIG. 8 is a side cross-sectional view of one end of a pouch described herein with the tobacco product being inserted into the tubular enclosure.

FIG. 9 is a side view of a pouch as described herein where second end is tubular end of the pouch is partially clamped.

FIG. 10 is a side view of a pouch as described herein where first the elastomeric thread is stretched and then the second end is sealed.

FIG. 11 is a side view of a pouch after each sealed end is sheared from the inside of the clamp as described herein upon final assembly.

DETAILED DESCRIPTION

Figure 1:
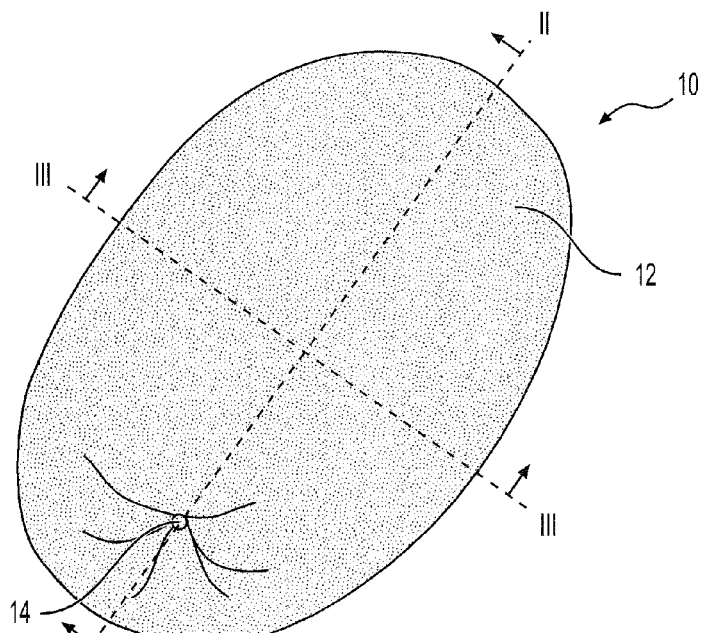
FIG. 1 is a perspective view of a seamless oral pouch as described herein.

The pouch product described herein is formed from tubular hosiery and includes plant material contained within the tubular enclosure formed by the tubular hosiery. The pouch enclosure formed from the tubular hosiery is seamless or has fewer seams than conventional tea-bag oral pouches. Opposite ends of the tubular enclosure are closed and connected to a central elastic thread that draws the closed ends of the tubular enclosure into the tubular body, thereby removing the end closure seams from the outside of the pouch. The tubular enclosure itself may or may not have a longitudinal seam on one side depending on the manufacture of the hosiery web enclosure material.

The tubular enclosure discussed herein is formed from a hosiery material as compared with the nonwoven and cellulosic webs found with many conventional pouches. Hosiery is a term that often describes garments worn directly on the legs and feet and are also generically known as hose. Before modern methods of knitting and weaving were developed, hosiery was woven in a sheet just like any other fabric, then fitted, cut and sewn into a tube with a seam along one side. Normally, this seam ran up the back of a user's leg from the waist or hip down to the bottom of the foot. Modern seamless hosiery is made in the weft knitting process where stitches are connected to each other horizontally resulting in a finished product with great flexibility that can fit nearly any shape of an object placed inside of it. Knitting machines, such as those for instance manufactured by Lonati, knit hosiery on a circular cylinder generally with 3"-4½" diameters with approximately 400 needles. For the tubular hosiery enclosure described herein to have no seams, a knitting machine with generally a ¼" to ¾" diameter cylinder must be developed. Until that is accomplished, readily available 3"-4½" knitted hosiery can be used, cut and sewn together resulting generally in a tubular enclosure diameter ranging from about ¼" to ¾", or alternatively, about ⅜"-½", with a longitudinal seam on its side length.

The hosiery material described herein refers to a knitted web of material. In its most basic sense, knitting creates multiple loops of yarn or thread called stitches in a line or tube. A knitted material consists of a number of consecutive rows of interlocking loops. Like weaving generally, knitting is a technique for producing a two-dimensional material made from a one-dimensional yarn or thread. In weaving, threads are always substantially straight, running parallel either lengthwise or crosswise. In contrast, the yarn or thread in a knitted material follows a meandering path or course. Symmetrical loops are formed and interlocked above and below the meandering path of the yarn. These meandering, interlocking loops can be easily stretched in different directions giving knit materials much more elasticity than woven fabrics.

Numerous dimensions and sizes of hosiery thread materials may be used to form the oral pouch described herein. In one example, sheer hosiery is made primarily from nylon with some spandex. A typical blend is about 90% nylon and 10% spandex ("spandex" is used generally herein to refer to an elastomeric, polyester-polyurethane copolymer or other elastomer). The thinnest and most transparent style of hosiery is commonly referenced as "sheer hosiery" and is made from 5 to 40 denier nylon. Another benefit with using a nylon thread is that the nylon material does not absorb saliva as compared with conventional cellulose fiber pouch materials. This sheerness of the nylon thread, in this example, delivers its user an intimate relationship with its filling; to be as thin as possible for the users saliva to be absorbed through the hosiery by the filling and to be very flexible so the user can frequently reshape it like a dip of snuff, but strong enough to not rupture during use. All materials (nylon, silk, spandex and elastomeric thread) in the oral pouch are of food and/or medical grade and approved for oral use.

When knitted, the hosiery can be made from one spool of nylon and one spool of spandex or many spools of each. Of course the hosiery could be formed of other natural and synthetic polymer threads including silk, cellulose, polyester, polyethylene and others. Nylon and spandex are simple common thread examples. The nylon and spandex may be of similar, or alternatively different, deniers. For instance, each of the knit yarn threads may be from about 5 to about 40 denier, or alternatively about 8 to about 30 denier, or still further about 12 to about 25 denier. For instance, a 20 denier nylon may be knitted with an 18 denier spandex both of a similar color. The deniers of the nylon and spandex can move into greater ranges to maximize performance and texture within the oral cavity. Many different color yarns/threads of nylon and spandex could alternatively also be used to create custom weave patterns and color patterns for specific brands as is commonplace in the athletic sock industry. Different deniers of threads including nylon and spandex can also be used to enhance patterns and color combinations as is commonplace, for instance, in the intimate undergarment industry.

While a knitted hosiery pouch is mostly described herein, alternatively, a woven or non-woven material could be used. The woven or non-woven pouch material would be made with fibers as described herein. Additional fibrous material could be used. Importantly, the pouch material needs to be pliable and porous. As will be explained, the pouch material is knotted or bound on opposite ends with an elastomeric thread that draws in the bound or knotted ends of the tubular pouch. In the alternative examples of a woven or non-woven fabric pouch material, it is also preferred that the pouch material be formed of a continuous tubular web. This would result in a seamless pouch. However, alternatively, a flat web may be trimmed and connected along a single, longitudinal seam that would result in a relatively more seamless pouch product than existing conventional pouch products.

Whether the oral pouch material is a knitted hosiery material or a woven or non-woven material, the specific fibers that are used to form the tubular web enclosure are chosen to have a preferred porosity and density for purposes of the flexibility and feel of the pouch in a user's mouth.

Additionally, some of the yarns or fiber threads used may be coated or impregnated with flavorings (such as vanilla), stimulants (such is nicotine, caffeine or decarbolized THC) or pharmaceuticals for manufacturers to further distinguish and enhance the performance of their products. Suitable flavorants include any flavorants commonly used in foods, confections, smokeless tobacco products, tobacco articles, and/or other oral products. Exemplary flavorants include, but are not limited to, berry flavors such as pomegranate, acai, raspberry, blueberry, strawberry, boysenberry, and/or cranberry. Other suitable flavorants include, without limitation, any natural or synthetic flavor or aroma, such as menthol, peppermint, spearmint, wintergreen, bourbon, scotch, whiskey, cognac, hydrangea, lavender, chocolate, licorice, citrus and fruit flavors, such as apple, peach, pear, cherry, plum, orange, lime, grape, and grapefruit, gamma octalactone, vanillin, ethyl vanillin, breath freshener flavors, butter, rum, coconut, almond, pecan, walnut, hazelnut, French vanilla, macadamia, sugar cane, maple, cassis, caramel, banana, malt, espresso, kahlua, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, peanut oil, lemon oil, ginger oil, balsamic vinegar, rice wine vinegar and red wine vinegar. Particularly preferred flavorants include mint oils such as peppermint oil, spearmint oil, wintergreen oil and combinations thereof. Preferably, the mint oils are added to the web and/or the filling material. Preferably, the flavorants are added to the oral pouch product in an amount of about 0.1% to about 10% by weight based on the weight of the oral pouch product. More preferably, the flavorants are added to the oral pouch product in an amount of about 1% to about 5% by weight based on the weight of the oral pouch product. The amount of flavorant added can depend on the flavorant used as some flavorants are more potent than others and therefore can provide adequate flavoring in smaller amounts.

The flavorants can be applied to the filling material and/or web by spraying, coating, immersing, embossing, and/or dispersing the flavorants into or onto the filling material and/or web. In an embodiment, the flavorants are added in the form of spray dried flavorants, essential oils, encapsulated flavorants, coacervated flavorants, colloidal encapsulated flavorants, suspensions, and/or solutions.

In an embodiment, suitable sweeteners include, without limitation, monosaccharides, disaccharides, and polysaccharides, xylose, ribose, sucrose, maltose, mannitol, sorbitol, xylitol, fructose, glucose, mannose, sucralose, and combinations thereof. The amount of sweetener added to the oral pouch product can vary based on the sweetener and/or combination of sweeteners used. For example, sucralose may be added to the oral pouch product in an amount of about 0.1% to about 3% by weight based on the weight of the oral pouch product. More preferably, sucralose may be added to the oral pouch product in an amount of about 0.5% to about 1.5% by weight based on the weight of the oral pouch product. Also for example, sugar can be added in an amount of about 5% to about 25% by weight based on the weight of the oral pouch product. More preferably, sugar is added in an amount of about 10% to about 20% by weight based on the weight of the oral pouch product.

A single yarn impregnated with flavorants, sweeteners or other chemicals or a combination of single yarns with different chemicals impregnated in each may be woven along with other non-impregnated yarns to comprise the pouch.

In a preferred embodiment, the oral pouch product is sized and configured to fit comfortably in a user's mouth, preferably between the cheek and gum. A user can suck, chew, or otherwise orally manipulate the oral tobacco pouch product to release the flavors contained therein.

The entire oral pouch product may weigh about 0.1 g to about 5.0 g. These ranges for weight can be further restricted to (a) about 0.1 g to about 1.0 g, (b) about 1.0 g to about 2.0 g, (c) about 2.0 g to about 3.0 g, (d) about 3.0 g to about 4.0 g or (e) about 4.0 g to about 5.0 g.

At least one flavorant may be spearmint oil added as a coating to the web to speed up flavor delivery upon placement of the oral pouch product in a user's mouth. Not wishing to be bound by theory, it is believed that the use of some flavorants in a coating, and liquid flavorants in particular (which have an affinity for the web), is preferred because some flavorants do not sufficiently migrate from the filling material to the wrapper and/or user. Thus, some flavorants, such as peppermint oil, may migrate over time from the filling material such that the flavorant is only added as a coating if desired, while other flavorants that are less prone to migrate are preferably added as a coating to the web enclosure. In addition, dry flavorants and/or sweeteners in either liquid or dry form may be applied to the web as a coating because such flavorants and/or sweeteners are not believed to migrate over time.

The elastomeric thread used to pull the two ends of the tubular enclosure together may be a natural rubber elastic, spandex, synthetic elastomeric polymers or comprised of other elastomers. The material will have a low modulus resulting in a high elastic limit. The diameter and length of a specific tubular enclosure and the amount and density of the proposed filling material will determine the modulus of the elastomeric thread used for that specific pouch design. The seal at each end of the material will in one example heat weld with the nylon/spandex hosiery blend. In another example it may be sewn, stitched or knotted.

Figure 10:
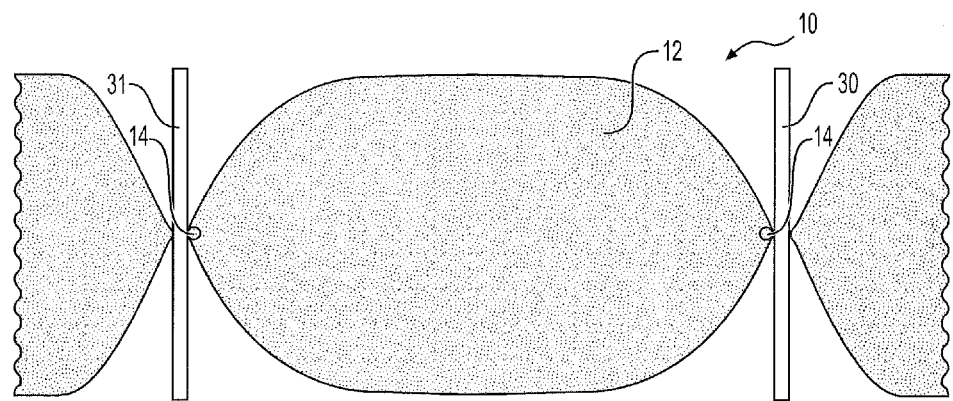
Figure 12:
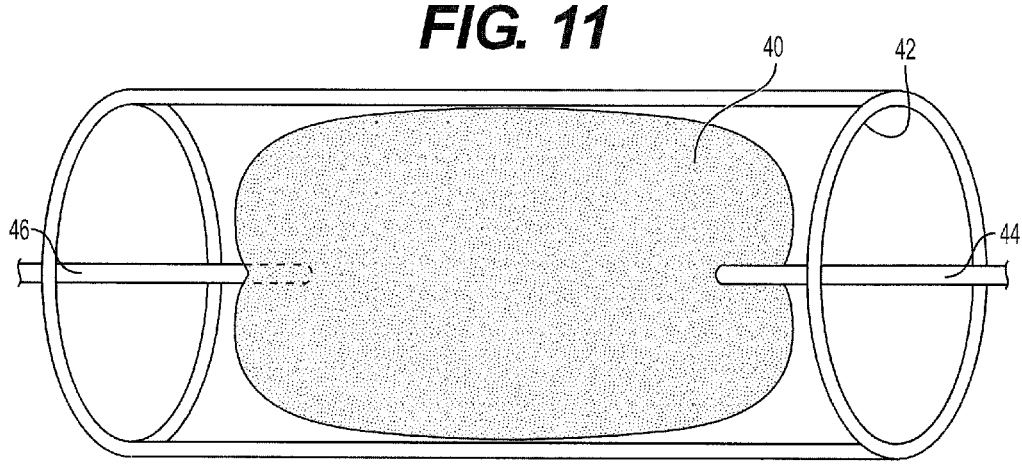
FIG. 12 is an alternative example of the pouch described herein being positioned in a hard tubular structure in order to impart a consistent tubular shape to the finished pouch.

Alternatively, the pouch may be formed without any thread or elastomeric thread in the center of the pouch and connected to the sealed ends. For instance, the pouch would appear just as it does in FIG. 1, but with no thread inside that connects the ends together. In one example, this could be accomplished wherein the sealed ends are physically tamped into the tubular pouch body as illustrated in FIG. 12. Still further alternatively, one or both of the sealed ends may rest outside of the tubular pouch body as illustrated in FIG. 10 (except without an internal elastic thread). The ends may or may not be connect to each other by any thread or elastic thread.

The oral pouch described herein is to be used as an embodiment for manufacturers of products to be enjoyed in the mouth and that may or may not have additive chemicals such as nicotine, caffeine or decarbolized THC and that additionally may or may not have pharmaceuticals that will enter the bloodstream via absorption through tissues in the oral cavity. Snuff and snuss and mixtures thereof will be the primary filler in the embodiment. Tobacco may be blended with other fillers, such as coconut husks or plant pulp. Non-tobacco fillers may be blended with pharmaceuticals. Decarbolized marijuana and marijuana blends or decarbolized marijuana and tobacco blends may also be fillers. Any filler product with characteristics that can be dissolved with or imparted by saliva and then absorbed through oral tissues into the bloodstream and optionally have its flavors sensed on the tongue are intended for use with the oral pouch. Since the pouch can remain in the oral cavity for long periods of time without irritation while continuing to slowly leach out saliva laden with fillings flavors and chemicals, a wide range of applications exist. Furthermore, being able to remove the pouch from the mouth, store it safely and then insert it again in the mouth for another usage provides manufactures with a new range of use not presently existing with snuff, chewing gum or breath mints. This removal and re-use ability strengthens the confidentiality benefits of the invention. Hence, the pouch serves at least several purposes:

1. A better performing oral pouch than the present "tea bag pouch" as described herein, including, without limitation, a pouch that reduces gum irritation and displays greater formability to the oral cavity.
2. A new chemical delivery device for pharmaceutical manufacturers allowing users to take their medicine while freshening their breath and enjoying the pleasure of an oral fixation with the possible addition of stimulants such as nicotine, caffeine or decarbolized THC.
3. A new delivery device and method for freshening breath as opposed to chewing gum, lozenges, mints and sprays.
4. The hosiery or woven web enables the use of a multitude of colors, patterns, designs and logo indicia to be knitted into a display on the pouch. Manufacturers may brand the pouch itself or display other promotional or marketing indicia on the pouch web. Presently, it is believed that no teabag pouches display such indicia, but are instead a generic white or brown color.

The oral pouch can be produced in a range of sizes. It is believed that a popular size would be ½" in diameter and ¾" long. However, ¼" and ⅜" diameters with ½" to 1" lengths can be used to accommodate a user demands for a pouch that cannot be seen bulging the lip. Alternatively, a ¾" diameter with a 1" long pouch will be the "extra-large" type that dramatically bulges the lip. Alternatively, a ⅛" diameter by 2" long pouch may work well between the upper lip and gum, while the shorter and fatter pouches may work well between the lower lip and gum. The longer pouch used for the upper lip is designed to generally stay in place while the shorter (about 1" or less) are generally designed for either the upper or lower lip area and can either stay in place or be moved about. Since the pouch is seamless and flexible and can be made from a wide range of diameters and lengths of woven hosiery tube, each and every manufacturer of fillings will have the ability to determine precisely the dimensions desired for the delivery of their specific product.

In another example, it is possible to produce a pouch within a pouch. That is to produce the pouch described herein with an inner filling and then to insert that first completed pouch inside of a second pouch along with the same or another filling. This product ability provides manufactures of filling materials with an embodiment design capability to create new embodied products and to dramatically alter the performance of their fillings from that of single pouch embodiments.

The amount of tobacco, tobacco formulation or other non-tobacco filler contained within each pouch may vary from about 50 to 500 mg. In smaller embodiments, the dry weight of the tobacco formulation within each pouch is at least about 50 mg to about 150 mg. For a larger embodiment, the dry weight of the tobacco formulation or filler within each pouch preferably does not exceed about 300 mg to 500 mg.

In certain embodiments, a plurality of very small capsules, commonly referred to as "microcapsules" may be incorporated within the pouch. That is, at least one capsule within the tobacco formulation or filler may be of a microcapsule form. The number of microcapsules in the pouch may vary. The capsules may also be engineered to have delayed time-release attributes to extend the flavor enjoyment.

The present pouch may be packaged and stored in much the same manner that conventional types of smokeless tobacco products are stored and packaged. For example, a plurality of pouches may be contained in a low-profile cylindrical or rectangular container. Moist tobacco products may be refrigerated and relatively dry tobacco products may be stored under a relatively wide range of temperatures.

Turning now to the figures, in FIG. 1 there is a perspective view of an oral pouch 10. The oral pouch 10 is comprised of an outer web 12 made out of a hosiery material as discussed herein. The bound and sealed end 14 of the hosiery material 12 seals a filling material inside the pouch 10.

Figure 1A:
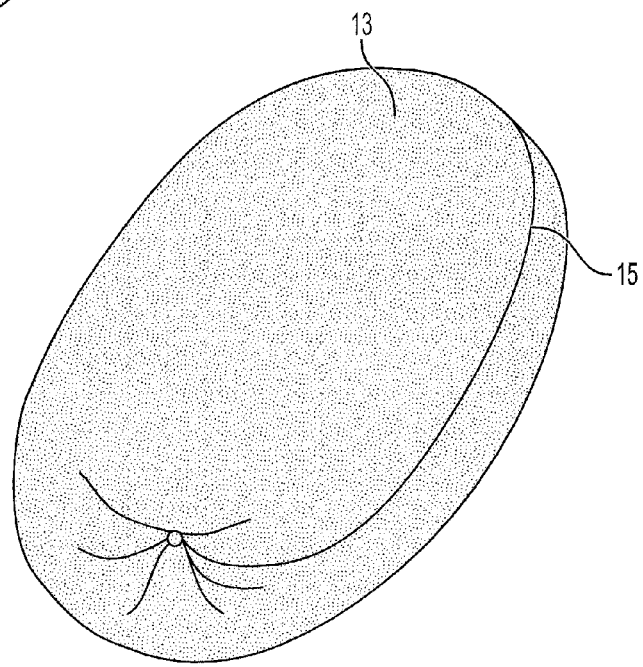
FIG. 1A is a perspective view of an alternative, single seam oral pouch as described herein.
Figure 2:
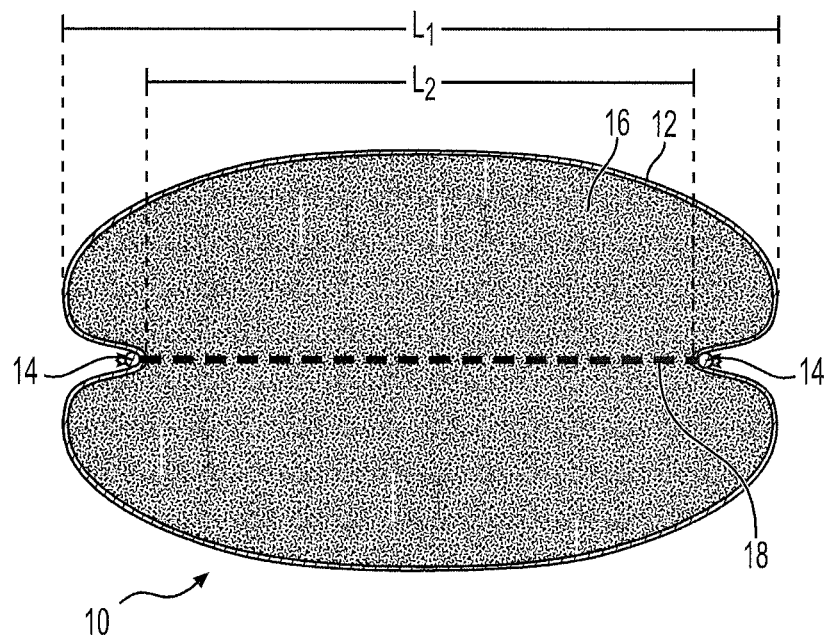
FIG. 2 is a side cross-sectional view of an oral pouch as described herein.

FIG. 2 is a side, cross-sectional view of the oral pouch 10. The outer hosiery web layer 12 is shown containing the filling material 16. The oral pouch 10 has a generally tubular shape. The sealed ends 14 are connected to opposite ends of an elastomeric thread 18 that passes through approximately the coaxial center of the tubular oral pouch 10. (Alternatively fixed, bound, knotted, or sealed are all terms that may be used to describe the closure at each end of the tubular oral pouch web.) Importantly, the elastic thread 18 draws the ends 14 of the hosiery web 12 so that they are inside the longitudinal length L1 of the entire oral pouch 10. In other words, the length L2 of the elastic thread 18 at rest is less than the length L1 of the tubular oral pouch 10. This way, assuming that the hosiery web 12 is seamless, the entire outer portion of the oral pouch 10 that would come in contact with a user's mouth is seamless. As explained earlier, a flat hosiery web 13 may alternatively be cut and formed into a tube having a single longitudinal seam 15 as shown in FIG. 1A.

Figure 3:
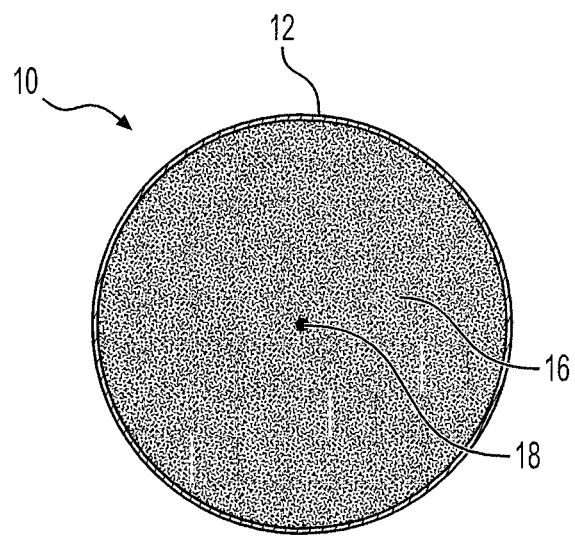
FIG. 3 is a longitudinal, cross-sectional view of an oral pouch as described herein.

FIG. 3 is a cross sectional end view of the oral pouch 10. The hosiery web enclosure 12 is generally circular in this cross section. The filling material 16 is contained therein. The elastic thread 18 is substantially in the coaxial center of the tubular oral pouch 10.

Figure 4:
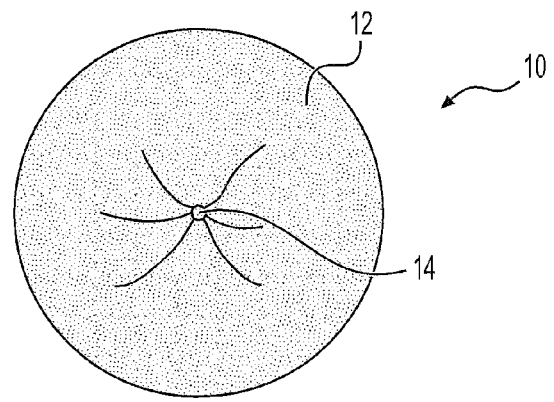
FIG. 4 is a side view of one of the ends of an oral pouch as described herein.

FIG. 4 is a simple end view of the oral pouch 10 which shows the hosiery web enclosure 12 and the sealed and bound end 14 thereof.

Figure 5:
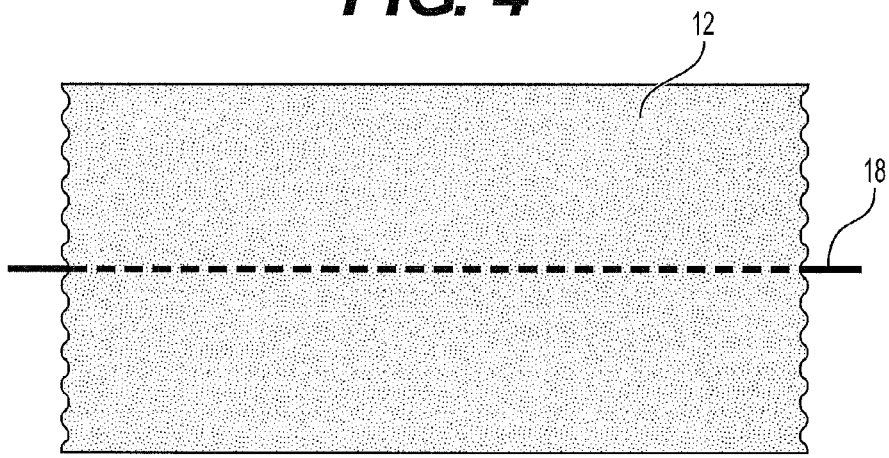
FIGS. 5-11 illustrate one example of the manufacture of an oral pouch as described herein.
Figure 6:
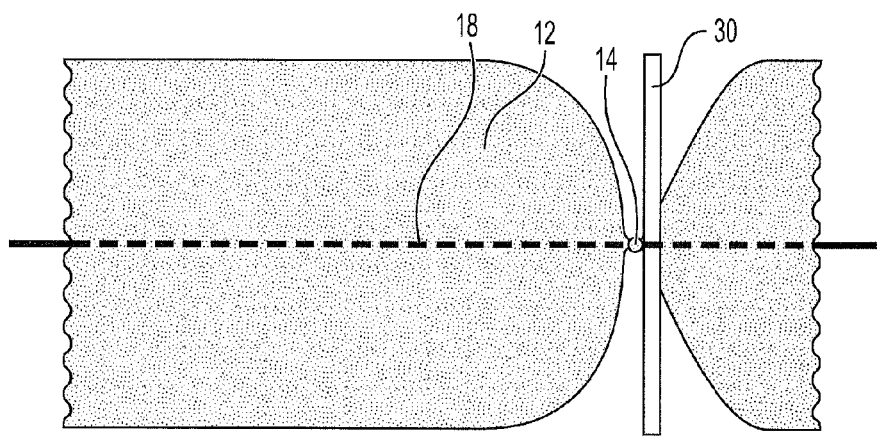

FIGS. 5-11 illustrate a very simple, manual method of making an oral pouch as described herein. Of course it is expected that the oral pouch may be assembled in many other ways that may be more efficient for manufacture in the future. In FIG. 5, there is a seamless tubular web of hosiery material 12 with an elastic thread 18 through the middle thereof. In FIG. 6, an end 14 is created by clamping web 12 with clamp 30 and sealing off one end of the tubular hosiery enclosure on the inside of the clamp. A first end of the elastic thread 18 is fixed to a first end 14 of the tubular enclosure 12 by heat weld, tying, knotting or other attachment means.

Figure 7:
Figure 8:
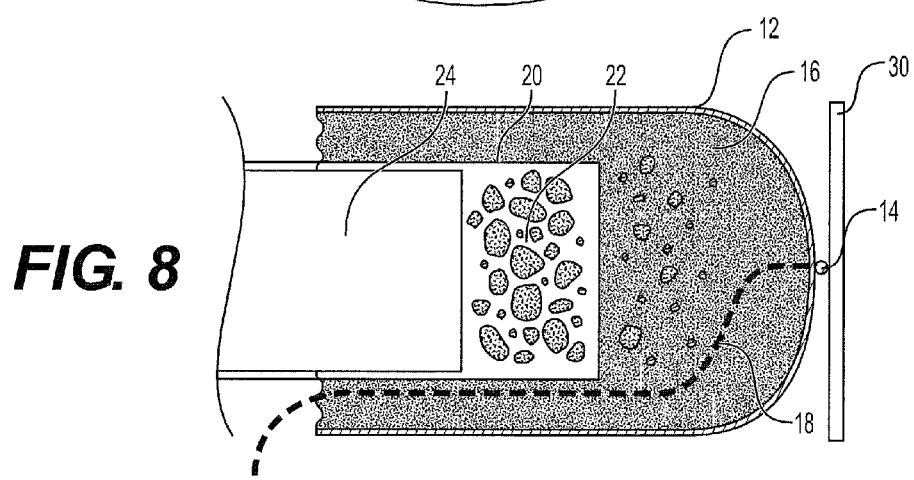
Figure 9:
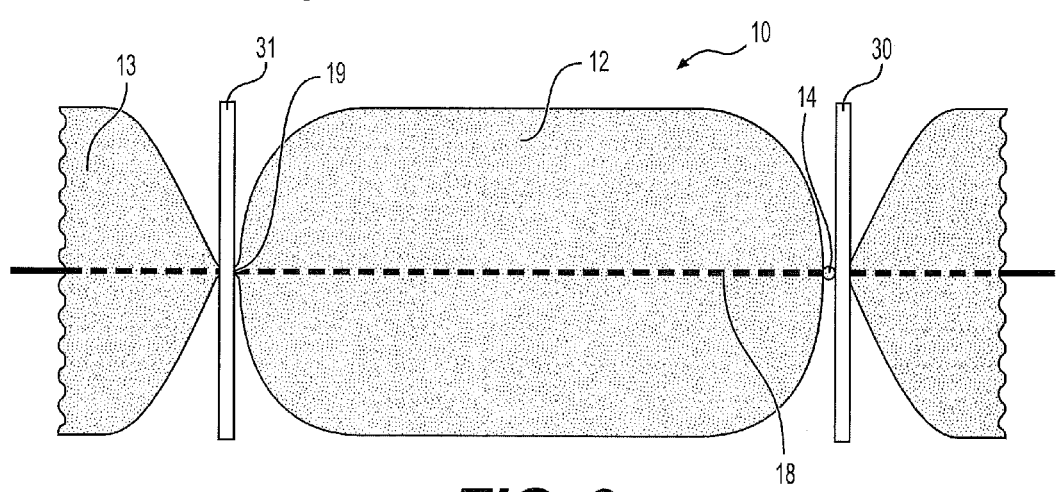
Figure 11:
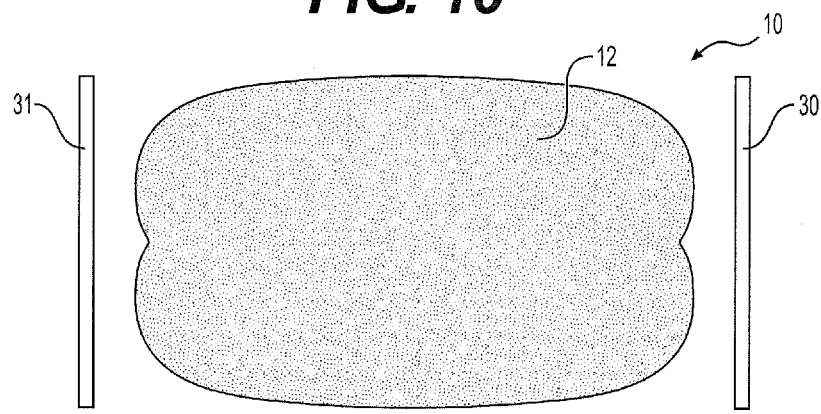

FIGS. 7 and 8 illustrate one way in which the pouch can be filled with, for example, a tobacco product. In FIG. 7, a hollow straw 20 is inserted into a can of loose tobacco snuff 22. The straw 20 is twisted back and forth and up and down so that tobacco is loaded into the end of the straw. The straw 20 is then placed inside the oral pouch 10, and specifically inside the tubular enclosure of hosiery web 12. A plunger 24 is inserted into the straw 20 to push out the tobacco material 22 into the sealed end of the hosiery web 12. As the tobacco 22 is plunged from the straw 20 into the hosiery web 12, the web slides along the straw until all of the tobacco load is deposited into the tubular web. In this illustrated example, the filling material 16 is comprised of the tobacco material 22. Once the tubular enclosure 12 is full, then the second end is partially clamped with a second clamp 31 as shown in FIG. 9. A second end of the elastic thread 18 is stretched and held by the clamp 31. The second end 19 of the elastomeric thread 18 is then stretched and fixed to hosiery at end 14. Each sealed end 14 is then sheared on its outside between it and the inside of the clamp. When each end is sheared as shown in FIG. 11, the thread 18 contracts pulling ends 14 closer together, tightening the web 12 around the inner filing 16, thereby resulting in the finished pouch 10.

For visual presentation purposes, FIG. 12 illustrates a rigid tube 42 in which an oral pouch 40 may be filled and formed. Rods 44 and 46 may be used to tamp each end of the pouch 40 in order to reproduce a consistent and uniform shape to the pouch product 40.

Other embodiments of the present invention will be apparent to those skilled in the art from consideration of the specification. It is intended that the specification and figures be considered as exemplary only, with a true scope and spirit of the invention being indicated by the following claims.

What is claimed is:

1. An oral pouch product comprising:
   a web defining an enclosure, wherein the enclosure has a tubular shape and thus forms a tubular enclosure having a first end and a second end;
   a loose filling material inside the enclosure, where the filling material comprises a plant material;
   wherein the web is comprised of hosiery material, and each of the first and second ends of the tubular enclosure is sealed;
   an elastomeric thread positioned inside the tubular enclosure, wherein the elastomeric thread is fixed on the first end to the tubular enclosure, and the elastomeric thread is fixed to the second end of the tubular enclosure opposite the first end of the tubular enclosure;
   wherein the sealed first and second ends of the tubular enclosure are closer together than a length of the tubular enclosure;
   whereby the sealed ends of the tubular enclosure are retained inside the tubular shape of the tubular enclosure.

2. An oral pouch product as described in claim 1, wherein the web is seamless.

3. An oral pouch product as described in claim 1, wherein the web is comprised of nylon.

4. An oral pouch product as described in claim 3, wherein the elastomeric thread is comprised of spandex.

5. An oral pouch product as described in claim 1, wherein the elastomeric thread is comprised of natural rubber.

6. An oral pouch product as described in claim 1, wherein the filling material is comprised of a plant material selected from the group consisting of tobacco, coconut husks, vegetable fibers, tea, herbs, spices, coffee, fruits, marijuana, marijuana derivatives and combinations thereof.

7. An oral pouch product as described in claim 1, wherein the filling material is comprised of a tobacco product.

8. An oral pouch product as described in claim 7, wherein the tobacco product is selected from the group consisting of snuff and snuss.

9. An oral pouch product as described in claim 1, wherein the filling material is comprised of non-plant material selected from the group consisting of nicotine, caffeine, decarbolized THC, flavorings and pharmaceuticals.

10. An oral pouch product as described in claim 1, wherein the tubular enclosure has a substantially round cross-section width of about one-quarter inch to three-quarters of an inch in diameter.

11. An oral pouch product as described in claim 1, wherein the tubular enclosure has a round cross-section width of about three-eighths to one half of an inch in diameter.

12. An oral pouch product as described in claim 1, wherein the longitudinal length of the tubular enclosure is about one-half to two inches.

13. An oral pouch product as described in claim 1, wherein the longitudinal length of the tubular enclosure is about three-quarters to one inch.

14. An oral pouch product as described in claim 1, wherein the dry weight of the filling material is about 50 mg to 500 mg.

15. An oral pouch product as described in claim 1, wherein the dry weight of the filling material is about 100 mg to 500 mg.

16. An oral pouch product as described in claim 3, wherein the nylon has a size of about five to forty denier.

* * * * *